United States Patent
Park et al.

(10) Patent No.: US 10,654,796 B2
(45) Date of Patent: May 19, 2020

(54) METHOD FOR PREPARING ALIPHATIC ISOCYANATE

(71) Applicant: HANWHA CHEMICAL CORPORATION, Seoul (KR)

(72) Inventors: Ju Young Park, Daejeon (KR); Cho Hee Ahn, Seoul (KR); Seung Won Chae, Suncheon-si (KR); Jeon Sik Kim, Seoul (KR); Sang Hyun Cho, Daejeon (KR)

(73) Assignee: HANWHA CHEMICAL CORPORATION, Seoul (KR)

( * ) Notice: Subject to any disclaimer, the term of this patent is extended or adjusted under 35 U.S.C. 154(b) by 0 days.

(21) Appl. No.: 16/469,224

(22) PCT Filed: Dec. 6, 2017

(86) PCT No.: PCT/KR2017/014240
§ 371 (c)(1),
(2) Date: Jun. 13, 2019

(87) PCT Pub. No.: WO2018/124526
PCT Pub. Date: Jul. 5, 2018

(65) Prior Publication Data
US 2020/0102268 A1     Apr. 2, 2020

(30) Foreign Application Priority Data
Dec. 29, 2016 (KR) .................. 10-2016-0182925

(51) Int. Cl.
*C07C 263/10* (2006.01)
(52) U.S. Cl.
CPC ................ *C07C 263/10* (2013.01)

(58) Field of Classification Search
CPC ................................... C07C 263/10
See application file for complete search history.

(56) References Cited

U.S. PATENT DOCUMENTS

| 5,196,572 A | 3/1993 | Okawa et al. |
| 2016/0200938 A1* | 7/2016 | Berger ............... C08G 18/6674 428/423.4 |
| 2017/0101368 A1* | 4/2017 | Knauf .................. C07C 263/10 |

FOREIGN PATENT DOCUMENTS

| CA | 2010224 | * 8/1990 | ........... C07C 263/10 |
| EP | 0384463 | 8/1990 | |
| JP | 2008-056662 | 3/2008 | |
| KR | 10-1994-0001948 | 3/1994 | |
| KR | 10-0953019 | 4/2010 | |
| KR | 10-1318828 | 10/2013 | |
| KR | 10-1392435 | 5/2014 | |
| KR | 10-2016-0047141 | 5/2016 | |
| KR | 10-2016-0051814 | 5/2016 | |
| KR | 10-2016-0137545 | 11/2016 | |
| WO | 2008-069256 | 6/2008 | |
| WO | 2015-155365 | 10/2015 | |

OTHER PUBLICATIONS

WIPO, A PCT Search Report & Written Opinion of PCT/KR2017/014240 dated Mar. 21, 2018.

* cited by examiner

*Primary Examiner* — Yate' K Cutliff
(74) *Attorney, Agent, or Firm* — Lex IP Meister, PLLC

(57) ABSTRACT

Provided is a method capable of preparing high-purity aliphatic isocyanate, particularly, xylylene isocyanate in a high yield in a simple manner without an additional separate process, wherein when aliphatic isocyanate is prepared using phosgene, a side-reaction inhibitor capable of inhibiting side-reactions is introduced during phosgenation.

12 Claims, No Drawings

METHOD FOR PREPARING ALIPHATIC ISOCYANATE

TECHNICAL FIELD

Cross-Reference to Related Application(S)

This application claims priority benefits from Korean Patent Application No. 10-2016-0182925, filed on Dec. 29, 2016, the entire contents of which are fully incorporated herein by reference.

The present invention relates to a method for preparing high-purity aliphatic isocyanate, and more particularly, a method for preparing high-purity aliphatic isocyanate including aliphatic polyisocyanate.

BACKGROUND ART

Xylylene diisocyanate (hereinafter, referred to as XDI) is classified into aliphatic isocyanate, even though it contains an aromatic ring, and is a very useful compound as a raw material for polyurethane-based materials, polyurea-based materials, or polyisocyanurate-based materials in chemical, resin, and paint industries.

Commonly, aliphatic isocyanate is prepared by a phosgenation process of reacting a raw material amine with phosgene. For example, XDI is prepared by reacting xylylene diamine (hereinafter, referred to as XDA) with phosgene. However, a side reaction frequently occurs during phosgenation for the preparation of XDI, because of high reactivity of the amino group, similar to the characteristic of aliphatic isocyanate. Impurities generated by the side reaction affect a production reaction of a polyurethane resin to generate a problem of quality deterioration of the resin.

Therefore, many methods of preparing high-purity XDI by reducing the content of the generated impurities have been studied and proposed.

Specifically, Korean Patent Publication No. 1994-0001948 discloses a method for preparing high-purity XDI by using an ester-based compound such as amyl acetate or hexyl acetate as a reaction solvent during preparation of xylylene diisocyanate by reaction of xylylene diamine or a hydrochloride thereof with phosgene. However, this method is problematic in that the solvent is expensive and purity and yield are still low.

Korean Patent No. 0953019 discloses a method for preparing isocyanate by phosgenation of amine hydrochloride which is prepared by a salt-forming process of reacting a linear or cyclic aliphatic amine with hydrogen chloride, wherein a pressure is applied during the salt-forming process in order to solve the transfer problem of amine hydrochloride.

Further, as a non-phosgenation method of using no phosgene, Korean Patent No. 1318828 discloses a method for preparing xylylene diisocyanate through non-phosgenation, wherein a diamine compound is reacted with alkyl chloroformate or dialkyl carbonate to prepare biscarbamate, which is then subjected to decomposition, thereby degrading and removing alcohol having a relatively low boiling point. However, as compared with the phosgenation method, this method is disadvantageous in terms of cost, and its application to industrial mass-production is difficult.

U.S. Pat. No. 5,196,572 also discloses a method for preparing xylylene diisocyanate through decomposition of carbamate. However, as compared with the phosgenation method, this method is also disadvantageous in terms of cost, its application to industrial mass-production is difficult, and its yield and selectivity are very low.

DETAILED DESCRIPTION OF THE INVENTION

Technical Problem

The present invention provides a method capable of preparing high-purity aliphatic isocyanate in a high yield in a simple manner without an additional separate process, wherein when aliphatic isocyanate is prepared using phosgene, a side-reaction inhibitor is introduced during phosgenation.

Technical Solution

According to one embodiment of the present invention, provided is a method for preparing aliphatic isocyanate, the method including the step of reacting aliphatic amine or a salt thereof with phosgene in the presence of a compound of the following Chemical Formula 1:

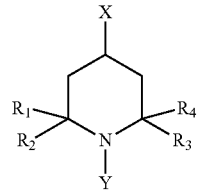

[Chemical Formula 1]

in Chemical Formula 1, $R_1$ to $R_4$ are each independently a $C_{1\sim12}$ hydrocarbyl group, X is hydrogen, a hydroxyl group, or an acetamido group, and Y is an oxyl (O•) group or a $C_{1\sim20}$ hydrocarbyloxy group.

Advantageous Effects

According to a preparation method of the present invention, high-purity aliphatic isocyanate may be prepared in a high yield through a simple preparation process.

DETAILED DESCRIPTION OF THE EMBODIMENTS

The terminology used herein is for the purpose of describing exemplary embodiments only and is not intended to be limiting of the invention. The singular forms are intended to include plural forms as well, unless the context clearly indicates otherwise. It will be understood that the term "including", "constituting", or "having", when used in this specification, specify the presence of stated features, integers, steps, components, or combinations thereof, but do not preclude the presence or addition of one or more other features, integers, steps, components, or combinations thereof.

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

Hereinafter, the present invention will be described in more detail.

Preparation of aliphatic isocyanate by phosgenation is commonly performed by reaction of aliphatic amine and phosgene, and at this time, monoisocyanates, etc. may be produced as side-products. For example, in the case of preparation of xylylene diisocyanate (XDI) as the aliphatic isocyanate, phosgene reacts with an amino group of aliphatic amine to remove hydrogen chloride and to produce carbamoyl chloride during phosgenation of xylylene diamine and phosgene. The carbamoyl group of the produced carbamoyl chloride reacts to form an isocyanate group while further removing hydrogen chloride, thereby forming xylylene diisocyanate. After completion of the reaction, the produced hydrogen chloride and remaining phosgene are generally removed together with inert gas by distillation, and as a result, they are separated from the produced xylylene diisocyanate. In this regard, since the amino group in the aliphatic amine, i.e., xylylene diamine is highly reactive, it causes side reactions during synthesis. In particular, the side reactions produce impurities including monoisocyanate-based compounds such as EBI (ethylbenzyl isocyanate), or CMBI (chloromethylbenzyl isocyanate), which influence reactivity of xylylene diisocyanate, and as a result, urethanation is inhibited and quality of produced polyurethane is deteriorated. In addition, there is no significant difference in a boil point and other physical properties between the produced monoisocyanate and aliphatic isocyanate including xylylene diisocyanate, and therefore, its separation is difficult and requires high cost.

In the present invention, accordingly, when aliphatic isocyanate is prepared, 2,2,6,6-tetramethylpiperidine-1-oxyl (TEMPO)-based compound is introduced as a side-reaction inhibitor to inhibit side-reactions at the phosgenation stage, thereby preparing high-purity aliphatic isocyanate in a simple manner without an additional separate process while reducing the content of impurities such as monoisocyanates, etc.

In other words, the method for preparing aliphatic isocyanate according to one embodiment of the present invention includes the step of reacting aliphatic amine or a salt thereof with phosgene in the presence of a compound of the following Chemical Formula 1:

[Chemical Formula 1]

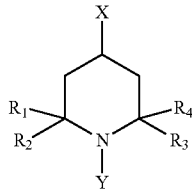

in Chemical Formula 1, $R_1$ to $R_4$ are each independently a $C_{1-12}$ hydrocarbyl group, X is hydrogen, a hydroxyl group, or an acetamido group, and Y is an oxyl (O•) group or a $C_{1-20}$ hydrocarbyloxy group.

The compound of Chemical Formula 1 serves to eliminate hydrogen of amine or the intermediate carbamoyl chloride during phosgenation, thereby promoting the forward reaction and suppressing the side reaction, and as a result, production of monoisocyanates as by-products is inhibited.

Specifically, $R_1$ to $R_4$ in Chemical Formula 1 may be each independently selected from the group consisting of a $C_{1-12}$ alkyl group, a $C_{3-12}$ cycloalkyl group, a $C_{6-12}$ aryl group, a $C_{7-12}$ arylalkyl group, a $C_{7-12}$ alkylaryl group, and a $C_{2-12}$ alkenyl group, more specifically, a $C_{1-4}$ alkyl group, and much more specifically, a methyl group.

Further, Y in Chemical Formula 1 may be an oxyl radical, a $C_{1-12}$ alkoxy group, or a $C_{6-12}$ aryloxy group, and more specifically, an oxyl group.

Specific examples of the compound of Chemical Formula 1 may include 2,2,6,6-tetramethylpiperidine-1-oxyl (TEMPO), 4-hydroxy-2,2,6,6-tetramethylpiperidine 1-oxyl (hereinafter, referred to as 4-hydroxy TEMPO), 4-methoxy-2,2,6,6-tetramethyl-piperidine 1-oxyl (4-methoxy-TEMPO), 2,2,6,6-tetramethyl-4-benzyl oxypiperidine-1-oxyl (4-benzyloxy-TEMPO), or 4-acetamido-2,2,6,6-tetramethylpiperidine 1-oxyl (hereinafter, referred to as 4-acetamido TEMPO), etc., and any one thereof or a mixture of two or more thereof may be used.

In terms of suppressing side reactions and improving the preparation yield of high-purity aliphatic isocyanate thereby, the compound of Chemical Formula 1 may be specifically a compound of Chemical Formula 1, wherein $R_1$ to $R_4$ are each independently a $C_{1-4}$ alkyl group, X is hydrogen, a hydroxyl group, or an acetamido group, and Y is an oxyl radical, and more specifically, the compound of Chemical Formula 1 may be TEMPO, 4-hydroxy TEMPO, or 4-acetamido TEMPO, and any one thereof or a mixture of two or more thereof may be used.

The compound of Chemical Formula 1 may be added in a ratio of 0.05 moles to 2 moles with respect to 100 moles of the aliphatic amine or the salt thereof. When the use amount is less than 0.05 moles, the effect of inhibiting the side reaction may be insignificant, and thus it is difficult to prepare high-purity aliphatic isocyanate. When the use amount is more than 2 moles, there are concerns about generation of the side reaction and reduction of the yield according to excess use of the compound of Chemical Formula 1. The compound of Chemical Formula 1 may be added in a ratio of more specifically 0.1 mole to 1 mole, much more specifically 0.15 moles to 0.8 moles with respect to 100 moles of the aliphatic amine or the salt thereof.

In the method for preparing aliphatic isocyanate according to one embodiment of the present invention, the phosgenation may be performed in an organic solvent having a boiling point of 120° C. or higher, and more specifically 120° C. to 170° C. When the phosgenation is performed in the solvent having a high boiling point, high-purity aliphatic isocyanate may be prepared in a high yield.

Further, the organic solvent may include at least one of an aromatic hydrocarbon-based organic solvent and an ester-based organic solvent.

The aromatic hydrocarbon-based organic solvent may be specifically a halogenated aromatic hydrocarbon-based organic solvent such as monochlorobenzene, 1,2-dichlorobenzene, 1,2,4-trichlorobenzene, etc.

The ester-based organic solvent may be specifically an aliphatic ester such as amyl formate, n-butyl acetate, isobutyl acetate, n-amyl acetate, isoamyl acetate, methylisoamyl acetate, methoxybutyl acetate, sec-hexyl acetate, 2-ethylbutyl acetate, 2-ethylhexyl acetate, cyclohexyl acetate, methylcyclohexyl acetate, benzyl acetate, ethyl propionate, n-butyl propionate, isoamyl propionate, ethyl acetate, butyl stearate, butyl lactate or amyl lactate, etc.; and an aromatic carboxylic acid ester such as methyl salicylate, dimethyl phthalate, methyl benzoate, etc.

More specifically, the organic solvent may include at least one of aromatic hydrocarbon-based organic solvents and ester-based organic solvents having a boiling point of 120°

C. or higher, or 120° C. to 170° C. among the above-described aromatic hydrocarbon-based organic solvents and ester-based organic solvents.

When the phosgenation is performed in the organic solvent, the aliphatic amine or salt thereof may be used at a concentration of 20 volume % or less. When the concentration of the aliphatic amine or salt thereof is more than 20 volume %, there is concern about precipitation of a large amount of amine hydrochloride. More specifically, the aliphatic amine or salt thereof may be used at a concentration of 1 volume % to 20 volume %, and much more specifically at a concentration of 5 volume % to 15 volume %.

Further, the aliphatic amine which is applicable to the method for preparing aliphatic isocyanate according to one embodiment of the present invention is not particularly limited, as long as it is amine having an aliphatic group. The aliphatic amine may be specifically linear or cyclic aliphatic amine, and more specifically, bifunctional or multifunctional linear or cyclic aliphatic amine containing two or more amino groups in the molecule. Specific examples thereof may include hexamethylenediamine, 2,2-dimethylpentanediamine, 2,2,4-trimethylhexanediamine, butenediamine, 1,3-butadiene-1,4-diamine, 2,4,4-trimethylhexamethylenediamine, 1,6,11-undecatriamine, 1,3,6-hexamethylenetriamine, 1,8-diisocyanato-4-isocyanatomethyloctane, bis(aminoethyl)carbonate, bis(aminoethyl)ether, xylylenediamine, α,α,α',α'-tetramethylxylylenediamine, bis(aminoethyl)phthalate, bis(aminomethyl)cyclohexane, dicyclohexylmethanediamine, cyclohexanediamine, methylcyclohexanediamine, dicyclohexyldimethylmethanediamine, 2,2-dimethyldicyclohexylmethanediamine, 2,5-bis(aminomethyl)bicyclo-[2,2,1]-heptane, 2,6-bis(aminomethyl)bicyclo-[2,2,1]-heptane, 3,8-bis(aminomethyl)tricyclodecane, 3,9-bis(aminomethyl)tricyclodecane, 4,8-bis(aminomethyl)tricyclodecane, 4,9-bis(aminomethyl)tricyclodecane, bis(aminomethyl)norbornene, etc., and any one thereof or a mixture of two or more thereof may be used. Meanwhile, in the present invention, xylylene diamine may be classified into aliphatic diamine.

Further, the aliphatic amine may be a sulfur-containing aliphatic amine such as bis(aminomethyl)sulfide, bis(aminoethyl)sulfide, bis(aminopropyl)sulfide, bis(aminohexyl)sulfide, bis(aminomethyl)sulfone, bis(aminomethyl)disulfide, bis(aminoethyl)disulfide, bis(aminopropyl)disulfide, bis(aminomethylthio)methane, bis(aminoethylthio)methane, bis(aminoethylthio)ethane, bis(aminomethylthio)ethane, 1,5-diamino-2-aminomethyl-3-thiapentane, etc.

The salts of the above-described aliphatic amines may also be used in the preparation of the aliphatic isocyanate according to one embodiment of the present invention. Specifically, hydrochlorides or carbonates of the above-described aliphatic amines may be exemplified.

Among the above-described aliphatic amines, xylylene diamine or a salt thereof may be applied to the method for preparing aliphatic isocyanate according to one embodiment of the present invention, thereby obtaining more excellent effect. Specifically, xylylene diamines (XDA) such as m-xylylene diamine, p-xylylene diamine, or o-xylylene diamine, XDA-HCl salts, or XDA carbonates etc. may be exemplified, and any one or more thereof may be used.

The aliphatic amine or salt thereof may be prepared according to a common method. Specifically, XDA-hydrochloride may be prepared by reacting XDA with anhydrous hydrochloric acid, and XDA-carbonate may be prepared by reacting XDA with carbonic acid.

In the method for preparing aliphatic isocyanate according to one embodiment of the present invention, the phosgenation may be performed by a direct phosgenation method of directly reacting aliphatic amine with phosgene (method 1); a method of reacting aliphatic amine with hydrochloric acid to produce aliphatic amine-hydrochloride, and then reacting the produced salt with phosgene (method 2); or a method of reacting aliphatic amine with carbonic acid to produce aliphatic amine-carbonate, and then reacting the produced salt with phosgene (method 3).

First, the direct phosgenation method of the method 1 may be performed by reacting aliphatic amine with phosgene in the above-described organic solvent in the presence of the compound of Chemical Formula 1. In this regard, the phosgene may be all introduced at the initial stage of the reaction, or part thereof may be introduced at the initial stage of the reaction, and then the remainder may be introduced in portions during the reaction.

More specifically, the method 1 may be performed by a first step of dissolving the compound of Chemical Formula 1 and part of phosgene in the organic solvent, and then introducing the aliphatic amine thereto; and a second step of introducing and reacting the remainder of the phosgene after completing the introduction of the aliphatic amine. In this regard, the first step is preferably performed at a temperature of −15° C. to −10° C. to prevent spillage of the highly toxic phosgene and to prevent rapid heat generation by introduction of the aliphatic amine. The phosgenation of the second step may be performed at 120° C. to 150° C. so that the reaction occurs at a proper reaction rate without concern about decomposition of the aliphatic amine. When the reaction is performed under the above-described temperature conditions, high-purity aliphatic isocyanate may be prepared in a high yield. Meanwhile, 50 wt % to 80 wt % or 55 wt % to 75 wt % of the total phosgene may be introduced at the initial stage of the reaction, and the remainder may be introduced after the reaction temperature is raised. In the method 1, the compound of Chemical Formula 1 may be used in an amount as described above. However, in terms of the excellent effects such as increase in purity and reduction of impurities by optimizing the amount of the compound of Chemical Formula 1 used in the above-described process, the compound of Chemical Formula 1 may be more specifically used in a molar ratio of 0.05 to 0.5 or 0.15 to 0.45 with respect to 100 moles of the aliphatic amine or the salt thereof. When the reaction is performed under the above conditions, purity may be increased and the content of monoisocyanate-based impurities may be greatly reduced.

The method 2 may be performed by reacting the aliphatic amine with hydrochloric acid in the organic solvent containing the compound of Chemical Formula 1 to produce aliphatic amine-hydrochloride, and then introducing phosgene thereto.

The production of aliphatic amine-hydrochloride may be performed at a temperature of 30° C. or lower, and the reaction after the introduction of phosgene may be performed at a temperature of 120° C. to 150° C. When the reactions are performed under the above temperature conditions, solubility of the aliphatic amine-hydrochloride may be increased, and decomposition of the aliphatic isocyanate may be prevented, thereby preparing high-purity aliphatic isocyanate in a high yield. In the method 2, the compound of Chemical Formula 1 may be used in an amount as described above. However, in terms of the excellent effects such as increase in purity and reduction of impurities by optimizing the amount of the compound of Chemical Formula 1 and the amount of the aliphatic amine used in the above-described process, the compound of Chemical Formula 1 may be more specifically used in a molar ratio of 0.15 to 0.8 with respect to 100 moles of the aliphatic amine or the salt thereof. In this regard, a concentration of the aliphatic amine in the organic solvent may be 8 volume % to 10 volume %. When the reaction is performed under the above conditions, purity may be increased and the content of monoisocyanate-based impurities may be greatly reduced.

The method 3 may be performed by reacting the aliphatic amine with carbonic acid in the organic solvent containing the compound of Chemical Formula 1 to produce aliphatic amine-carbonate, and then introducing phosgene thereto. The production of aliphatic amine-carbonate may be performed at a temperature of 30° C. or lower, and the reaction after the introduction of phosgene may be performed at a temperature of 120° C. to 150° C. When the reactions are performed under the above temperature conditions, solubility of the aliphatic amine-carbonate may be increased, and decomposition of the aliphatic isocyanate may be prevented, thereby preparing high-purity aliphatic isocyanate in a high yield. In the method 3, the compound of Chemical Formula 1 may be used in an amount as described above. However, in terms of the excellent effects such as increase in purity and reduction of impurities by optimizing the amount of the compound of Chemical Formula 1 and the amount of the aliphatic amine used in the above-described process, the compound of Chemical Formula 1 may be more specifically used in a molar ratio of 0.15 to 0.8 with respect to 100 moles of the aliphatic amine or the salt thereof. In this regard, a concentration of the aliphatic amine in the organic solvent may be 8 volume % to 10 volume %. When the reaction is performed under the above conditions, purity may be increased and the content of monoisocyanate-based impurities may be greatly reduced.

After completing the reaction according to the respective methods, a process of removing unreacted phosgene and hydrogen chloride gas by nitrogen bubbling and a process of removing the solvent by distillation may be further performed, and these processes may be performed according to common methods.

As described above, the method for preparing aliphatic isocyanate using the compound of Chemical Formula 1 as a side-reaction inhibitor may be performed to obtain high-purity aliphatic isocyanate in a high yield while reducing the content of impurities. Specifically, the aliphatic isocyanate prepared according to the present invention may have purity of 97% or more, and more specifically purity of 99% or more, as measured by gas chromatography (GC). The contents of EBI (ethylbenzyl isocyanate) and CMBI (chloromethylbenzyl isocyanate) measured by gas chromatography (GC) are 0.15% or less and 2.1% or less, respectively. More specifically, the content of EBI is 0.01% to 0.05%, and the content of CMBI is 0.1% to 0.6%, and the total content of monoisocyanates including EBI and CMBI is 2.15% or less, and more specifically, 0.1% to 0.7%.

When aliphatic isocyanate is prepared by the preparation method according to the present invention, no separate purification process is required, and therefore, loss of the product may be prevented.

The method for preparing aliphatic isocyanate according to one embodiment of the present invention is suitable for the preparation of common isocyanates including aliphatic isocyanate or aliphatic polyisocyanate. Specifically, the method may be suitable for the preparation of n-pentyl isocyanate, 6-methyl-2-heptane isocyanate, cyclopentyl isocyanate, hexamethylene diisocyanate (HDI), isophorone diisocyanate (IPDI), diisocyanatomethylcyclohexane (H6TDI), xylylene diisocyanate (XDI), diisocyanatocyclohexane (t-CHDI), di(isocyanatocyclohexyl)methane (H12MDI), etc., and particularly, for the preparation of xylylene diisocyanate (XDI).

Hereinafter, the actions and effects of the present invention will be described in more detail with reference to the specific embodiments. However, these embodiments are for illustrative purposes only, and the scope of the present invention is not intended to be limited thereby.

Analysis

Phosgenation products were analyzed by GC. GC used in the analysis was HP-6890, and FID was used for detection. A used column was DB-17 (30 m*0.25 mm*0.5 μm), a carrier gas was nitrogen (1.0 mL/min), an oven temperature was 80° C.→5° C./min→160° C. (8 min)→20° C./min→280° C. (18 min).

Example 1

410 g of monochlorobenzene was put in a 1 L flask, and cooled to −10° C. to −15° C. 0.4 g of 4-hydroxy TEMPO was added thereto and dissolved under stirring. The temperature of the flask was maintained at −10° C. to −15° C., and 100 g of liquid phosgene at low temperature (−10° C. to −15° C.) was introduced into the reactor, followed by stirring. A dry ice-acetone condenser was used from the point of injection of phosgene to the end of the reaction to prevent leakage of phosgene to the outside. 70 g of xylylenediamine (XDA) was dissolved in 80 g of monochlorobenzene, and then introduced into the flask using a dropping funnel. The temperature was maintained at −10° C. to −15° C. for cooling, since an exothermic reaction occurs when XDA is introduced. When the introduction of the XDA solution was completed, stirring was performed for 1 hour at the same temperature. Then, the internal temperature of the flask was heated to 130° C. When the internal temperature of the flask reached 130° C., 30 g of liquid phosgene was further introduced using a dropping funnel. The flask was allowed to maintain at 125° C. to 135° C., and stirring was further performed for 2 hours until the reaction solution became transparent. When the reaction solution became transparent, heating was stopped, and the solution was cooled to 80° C., followed by nitrogen bubbling. The resulting solution was recovered, and monochlorobenzene was removed by vacuum distillation, followed by GC analysis. As a result, XDI having purity of 99.17% was obtained.

Example 2

345 g of 1,2-dichlorobenzene was put in a 1 L flask, and cooled to −10° C. to −15° C. 0.24 g of 4-hydroxy TEMPO was added thereto and dissolved under stirring. The temperature of the flask was maintained at −10° C. to −15° C., and 61 g of liquid phosgene at low temperature (−10° C. to −15° C.) was introduced into the reactor, followed by stirring. A dry ice-acetone condenser was used from the point of injection of phosgene to the end of the reaction to prevent leakage of phosgene to the outside. 33 g of XDA was dissolved in 67 g of 1,2-dichlorobenzene, and then introduced into the flask using a dropping funnel. The temperature was maintained at −10° C. to −15° C. for cooling, since an exothermic reaction occurs when XDA is introduced. When the introduction of the XDA solution was completed, stirring was performed for 1 hour at the same temperature. Then, the internal temperature of the flask was heated to 130° C. When the internal temperature of the flask reached 130° C., 46 g of liquid phosgene dissolved in 59 g of 1,2-dichlorobenzene was further introduced using a dropping funnel. The flask was allowed to maintain at 125° C. to 135° C., and stirring was further performed for 2 hours until the reaction solution became transparent. When the reaction solution became transparent, heating was stopped, and the solution was cooled to 80° C., followed by nitrogen bubbling. The resulting solution was recovered, and 1,2-dichlorobenzene was removed by vacuum distillation, followed by GC analysis. As a result, XDI having purity of 97.7% was obtained.

Comparative Example 1

Reaction was performed in the same manner as in Example 1, except that 4-hydroxy TEMPO as an additive was not introduced.

In detail, 293 g of monochlorobenzene was put in a 1 L flask, and 31 g of phosgene was added thereto and dissolved. Then, 19.6 g of XDA was diluted with 57 g of monochlorobenzene, and the solution was introduced into the flask. The temperature was raised to 130° C., and 15.5 g of phosgene was further introduced. A subsequent process was performed in the same manner as in Example 1, and as a result, XDI having purity of 95.64% was obtained.

Comparative Example 2

Reaction was performed in the same manner as in Example 1, except that 1,2-dichlorobenzene was used as a solvent, and 4-hydroxy TEMPO as an additive was not introduced.

In detail, 345 g of 1,2-dichlorobenzene was put in a 1 L flask, and 37 g of phosgene was added thereto and dissolved. Then, 20 g of XDA was diluted with 67 g of 2-dichlorobenzene, and the solution was introduced into the flask. The temperature was raised to 130° C., and 15 g of phosgene dissolved in 59 g of 1,2-dichlorobenzene was further introduced. A subsequent process was performed in the same manner as in Example 1, and as a result, XDI having purity of 96.00% was obtained.

TABLE 1

|  |  | No. | | | |
| --- | --- | --- | --- | --- | --- |
|  |  | Example 1 | Comparative Example 1 | Example 2 | Comparative Example 2 |
| Use amount of 4-hydroxy TEMPO (based on 100 moles of XDA) | | 0.45 | — | 0.58 | — |
| XDI purity (%)*1 | | 99.17 | 95.64 | 97.7 | 96.00 |
| Contents of monoisocyanates (%)*1 | EBI*2 | 0.026 | — | 0.03 | 2.11 |
| | CMBI*3 | 0.54 | 2.60 | 2.04 | — |
| | others*4 | 0.066 | — | 0.07 | — |

*1 area % in GC analysis
*2 EBI (Ethylbenzylisocyanate), RT: 24.7~24.8 min
*3 CMBI (Chloromethylbenzyl isocyanate), RT: 25.7 min
*4 Not defined, RT: 26.0~26.1 min Example 3

471 g of 1,2-dichlorobenzene, 32.5 g of XDA, and 0.24 g of 4-hydroxy TEMPO were put in a flask, and anhydrous hydrochloric acid was introduced at a rate of 20 g/hr at room temperature (23±5° C.), followed by stirring. While introducing anhydrous hydrochloric acid, the temperature increased to 50° C. After injection for 4 hours, the produced salts were cooled at room temperature, and 43 g of phosgene was introduced into the reactor, and the reactor temperature was heated to 130° C. A dry ice-acetone condenser was used from the point of injection of phosgene to the end of the reaction to prevent leakage of phosgene to the outside. After the reactor temperature reached 130° C., the reactor temperature was maintained at 125° C. to 135° C. for 2 hours so that the reaction solution became transparent. After the solution became transparent, the internal temperature of the reactor was cooled to 80° C., and cooled under nitrogen bubbling. The reaction solution from which phosgene was removed was subjected to vacuum distillation to remove the solvent, followed by GC analysis. As a result, XDI having purity of 99.55% was obtained.

Comparative Example 3

Reaction was performed in the same manner as in Example 3, except that 4-hydroxy TEMPO as an additive was not introduced. As a result, XDI having purity of 98.38% was obtained.

TABLE 2

|  |  | Example 3 | Comparative Example 3 |
| --- | --- | --- | --- |
| Use amount of 4-hydroxy TEMPO (based on 100 moles of XDA) | | 0.58 | — |
| XDI purity(%)*1 | | 99.55 | 98.38 |
| Contents of monoisocyanates (%)*1 | EBI*2 | 0.034 | 0.46 |
| | CMBI*3 | 0.23 | 0.67 |
| | others*4 | 0.01 | 0.02 |

In Table 2, *1 to *4 are the same as defined above.

Examples 4 to 8

Each XDI was prepared by performing reaction in the same manner as in Example 3, except that XDA and 4-hydroxy TEMPO were used according to the amounts described in the following Table 3.

TABLE 3

|  |  | Example 4 | Example 5 | Example 6 | Example 7 | Example 8 |
| --- | --- | --- | --- | --- | --- | --- |
| Concentration of XDA (vol % in 1,2-dichlorobenzene) | | 8 | 11 | 11 | 8 | 8 |
| Use amount of 4-hydroxy TEMPO (based on 100 moles of XDA) | | 0.74 | 0.74 | 0.18 | 0.37 | 0.18 |
| XDI purity (%) *1 | | 99.66 | 99.11 | 99.56 | 99.33 | 99.75 |
| Contents of monoisocyanates (%) *1 | EBI *2 | 0.04 | 0.15 | 0.018 | 0.03 | 0.04 |
| | CMBI *3 | 0.19 | 0.28 | 0.31 | 0.49 | 0.11 |
| | others *4 | 0.01 | 0.18 | 0.012 | 0.02 | 0.004 |

In Table 3, *1 to *4 are the same as defined above.

The results of the above-described experiments confirmed that when the TEMPO-based compound is introduced during phosgenation of preparing aliphatic isocyanate using phosgene, high-purity aliphatic isocyanate may be prepared while reducing the content of impurities such as monoisocyanates, etc.

The invention claimed is:

1. A method for preparing aliphatic isocyanate, comprising: reacting aliphatic amine or a salt thereof with phosgene in the presence of a compound of the following Chemical Formula 1:

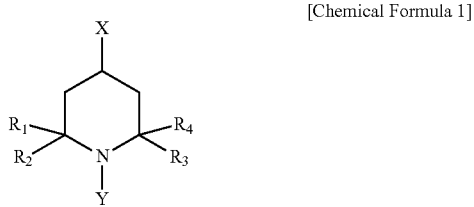

[Chemical Formula 1]

in Chemical Formula 1, $R_1$ to $R_4$ are each independently a $C_{1\sim12}$ hydrocarbyl group,
X is hydrogen, a hydroxyl group, or an acetamido group, and
Y is an oxyl (O•) group or a $C_{1\sim20}$ hydrocarbyloxy group.

2. The method of claim 1, wherein $R_1$ to $R_4$ in Chemical Formula 1 are each independently a $C_{1\sim4}$ alkyl group, X is hydrogen, a hydroxyl group, or an acetamido group, and Y is an oxyl group.

3. The method of claim 1, wherein the compound of Chemical Formula 1 is selected from the group consisting of 2,2,6,6-tetramethylpiperidine 1-oxyl, 4-hydroxy-2,2,6,6-tetramethylpiperidine 1-oxyl, and 4-acetamido-2,2,6,6-tetramethylpiperidine 1-oxyl.

4. The method of claim 1, wherein the compound of Chemical Formula 1 is used in a molar ratio of 0.05 to 2 with respect to 100 moles of the aliphatic amine or the salt thereof.

5. The method of claim 1, wherein the reacting with phosgene is performed in an organic solvent having a boiling point of 120° C. or higher.

6. The method of claim 1, wherein the reacting with phosgene is performed in an organic solvent selected from the group consisting of an aromatic hydrocarbon-based organic solvent, an ester-based organic solvent, and a mixture thereof.

7. The method of claim 1, comprising a first step of introducing the aliphatic amine or the salt thereof to a mixture which is prepared by dissolving the compound of Chemical Formula 1 and 50 wt % to 80 wt % of the total phosgene in an organic solvent at a temperature of −15° C. to −10° C.; and a second step of introducing and reacting the remainder of phosgene at 120° C. to 150° C. after completing the introduction of the aliphatic amine or the salt thereof.

8. The method of claim 7, wherein the compound of Chemical Formula 1 is used in a molar ratio of 0.05 to 0.5 with respect to 100 moles of the aliphatic amine or the salt thereof.

9. The method of claim 1, further comprising the step of preparing the salt of the aliphatic amine by reacting the aliphatic amine with hydrochloric acid or carbonic acid at a temperature of 30° C. or lower, before reacting with phosgene, wherein the reacting with phosgene is performed at 120° C. to 150° C.

10. The method of claim 9, further comprising the step of preparing aliphatic amine-hydrochloride by reacting the aliphatic amine with hydrochloric acid in an organic solvent containing the compound of Chemical Formula 1 at a temperature of 30° C. or lower, before reacting with phosgene, wherein the compound of Chemical Formula 1 is used in a molar ratio of 0.15 to 0.8 with respect to 100 moles of the aliphatic amine or the salt thereof, and a concentration of the aliphatic amine in the organic solvent is 8 volume % to 10 volume %.

11. The method of claim 1, wherein the aliphatic amine is xylylene diamine.

12. The method of claim 1, wherein purity of the aliphatic isocyanate is 97% or more, and a content of monoisocyanate including ethylbenzyl isocyanate and chloromethylbenzyl isocyanate is 2.15% or less.

* * * * *